United States Patent [19]
Abelson

[11] Patent Number: 4,981,871
[45] Date of Patent: Jan. 1, 1991

[54] TREATMENT OF OCULAR HYPERTENSION WITH CLASS I CALCIUM CHANNEL BLOCKING AGENTS

[76] Inventor: Mark B. Abelson, 26 Phillips St., Andover, Mass. 01810

[21] Appl. No.: 50,917

[22] Filed: May 15, 1987

[51] Int. Cl.$^5$ ............................................. A61K 31/275
[52] U.S. Cl. ...................................... 514/523; 514/913
[58] Field of Search ................................ 514/523, 913

[56] References Cited

U.S. PATENT DOCUMENTS

| | | | |
|---|---|---|---|
| 4,612,329 | 9/1986 | Itoh et al. | 514/523 |
| 4,686,217 | 8/1987 | Baxter et al. | 514/210 |

FOREIGN PATENT DOCUMENTS

| | | | |
|---|---|---|---|
| 1184497 | 3/1985 | Canada | 514/523 |

OTHER PUBLICATIONS

Chem. Abst., 86:183,208s (1977)-Green et al.
"Elevation of Intraocular Pressure by Calcium Channel Blockers", Jean F. Beatty, M.D., et al, Arch Ophthalmol, vol. 102, Jul. 1984, pp. 1072-1076.
"Anaesthetic Implications of Calcium Channel Blockers", Leonard C. Jenkins et al, Can Anaesth. Soc. J. 1985, 32:4, pp. 436-447.
"The Effect of a Calcium-Channel Blocking Agent on Intraocular Pressure", Monica L. Monica, M.D. et al, American Journal of Ophthalmology, Dec. 1983, p. 814.

*Primary Examiner*—Douglas W. Robinson
*Assistant Examiner*—Zohreh A. Fay
*Attorney, Agent, or Firm*—Weingarten, Schurgin, Gagnebin & Hayes

[57] ABSTRACT

Elevated intraocular pressure in a mammalian eye is lowered by administering to the eye an amount of a Class I calcium channel blocking agent effective to lower the elevated intraocular pressure. A preferred calcium channel blocking agent is verapamil and the preferred mode of administration is topical directly to the eye, e.g., with drops.

8 Claims, No Drawings

TREATMENT OF OCULAR HYPERTENSION WITH CLASS I CALCIUM CHANNEL BLOCKING AGENTS

BRIEF DESCRIPTION OF THE PRIOR ART

Chronically elevated intraocular pressure ("IOP") is a condition which can cause damage to the tissues of the eye leading ultimately to loss of vision in the affected eye. The disease is generally due to an impediment in the outflow of aqueous humor from the eye, and in most cases, the ultimate cause of the condition is unknown.

Nevertheless, in the common type of open-angle glaucoma, a number of types of drugs have been found useful in lowering and controlling elevated intraocular pressure. Timolol, an $alpha_1$- and $alpha_2$-adrenergic receptor antagonist, has been topically administered as a 0.25% and 0.5% solution. Betaxolol, a $beta_1$-adrenergic receptor antagonist, has been used topically as a 0.5% solution. Pilocarpine, a cholinergic stimulating drug, has been topically instilled into the eye in the form of the chloride or nitrate salt in a 1% to 4% solution, to control elevated intraocular pressure. Echothiophate iodide (0.03% and 0.06%), a cholinesterase antagonist, and epinephrine (1% and 2%), an alpha- and beta-adrenergic agonist, have also been used topically to control intraocular pressure. Acetazolamide, a carbonic anhydrase inhibitor, has been administered orally (250 mg tablets) to control intraocular pressure by decreasing the secretion of aqueous humor by the ciliary body. However, these drugs are not free from side effects, and some are effective only for a time, which can present problems since therapy must be lifelong.

Some interest has been expressed in the possibility of using calcium channel blocking agents for the treatment of glaucoma, but no demonstration has been made of their effectiveness.

Monica, M. L., et al, "The Effect of a Calcium-Channel Blocking Agent on Intraocular Pressure", American Journal of Ophthamology, December, 1983, p. 814, discloses that oral administration of nitrendipine to human subjects having mild hypertension but normal intraocular pressure produced a slight decrease in IOP.

Beatty, J. F., et al, "Elevation of Intraocular Pressure by Calcium Channel Blockers", Arch. Ophthalmol. 102. 1072-1076 (July, 1984), discloses that topical administration of the calcium channel blocker verapamil increased IOP in rabbits and humans having normal IOP.

Jenkins, L. C., et al, "Anaesthetic Implications of Calcium Channel Blockers", Can Anaesth. Soc. J. (Canada) 32 (4), pp. 436-447 (July, 1985) refers to the use of calcium channel blocking agents in treatment of ocular hypertension, but the reference is to the publication by Monica which, as discussed above, does not in fact disclose the use of calcium channel blocking agents in treatment of glaucoma.

It is an object of this invention to provide safe and effective treatment for glaucoma.

BACKGROUND OF THE INVENTION

This invention relates to reduction of intraocular pressure as found in ocular hypertension and glaucoma, by administration of particular calcium channel blocking agents, e.g., by topical administration directly to the eye.

SUMMARY OF THE INVENTION

A treatment has now been discovered which is effective in lowering intraocular pressure in patients suffering from ocular hypertension. According to the invention, ocular hypertension is treated by administering, e.g., topically, to the eye of a patient an amount of a Class I calcium channel blocking agent effective to reduce the elevated intraocular pressure.

DETAILED DESCRIPTION OF THE INVENTION AND PREFERRED EMBODIMENTS

Calcium channel blocking agents are a known group of drugs which act to inhibit transfer of calcium ions across the plasma membrane of cells. Because of their vasodilating effect, drugs of this group have come to be used for treatment of cardiac conditions such as angina. It has now been discovered that certain calcium channel blocking agents are capable of lowering elevated intraocular pressure when administered topically to the hypertensive eye in solution in a suitable ophthalmic vehicle. This effect is surprising, since, as reported by Beatty, verapamil, a well-known calcium channel blocking agent, does not lower the IOP of the normotensive eye.

The method of the invention comprises topical or systemic administration to a hypertensive mammalian eye of an amount of a Class I ("verapamil-like") calcium channel blocking agent effective to lower the IOP of the eye. As reported in TIPS, January 1987 (Vol. 8) at pages 4-5 and in the American Journal of Cardiology, 59, pages 3A-8A (1987), the World Health Organization has classified calcium channel blockers, also known as "calcium entry blockers" or "calcium antagonists" into six classes. Surprisingly, it has been found that diltiazem, a Class III agent, did not lower IOP in the hypertensive eye while verapamil, a Class I agent, did lower IOP. Therefore, the method of the present invention is the use of a Class I calcium channel blocker in the treatment of intraocular hypertension. Known Class I agents include verapamil, gallopamil and anipamil. Preferably, verapamil is used as the calcium channel blocker in the method of the invention.

The effective dose used in the method of the present invention will vary depending on the particular patient, the particular calcium channel blocking agent used and the mode of administration. However, the topical dose will typically range from about 10 micrograms to about 1 milligram per eye per day. The systemic dose will be less than about $\frac{1}{2}$ of the normal dose for vascular hypertension. Thus, a systemic dose will be about 1 to 100 mg per day for an average human for verapamil or a corresponding amount for other Class I calcium channel blockers having a different strength. Such a dose may be divided into 2-4 administrations per day.

The calcium channel blocking agent is administered topically in solution in a conventional aqueous pharmaceutically acceptable ophthalmic vehicle. The vehicle may be any such vehicle which is not incompatible with the drug, e.g., conventional physiological saline solution comprising 0.9% sodium chloride. A physiological saline buffered with a suitable buffering agent, e.g., a phosphate buffer, to maintain an approximately physiological pH is also a suitable vehicle. Typically the concentration of the calcium channel blocking agent in the vehicle will vary from about 0.1 mg/ml to about 5 mg/ml. Preferably, the concentration of the solution is adjusted to deliver the desired dose of active ingredient in a single drop, e.g., of about 40 microliters.

The calcium channel blocking agent may be delivered to the affected eye on a conventional dosage schedule determined by the duration of effectiveness of the particular agent. For example, the dosage regimen may comprise one drop instilled in the affected eye from one to four times a day.

Topical administration of the calcium channel blocker may also be carried out by insertion of a controlled release device into the eye as known in the art, e.g., in a polymeric matrix with slow release of the drug where the matrix either dissolves or is removed and replaced at a given interval.

Also, if used systemically, the calcium channel blocker may be used orally in the form of a tablet or capsule or transdermally, e.g., with a patch, both as known in the art.

EXAMPLE

This example illustrates the lowering of intraocular pressure in the hypertensive human eye.

A total of nine volunteers, six female and three male, in good health and not receiving any ocular medication, participated in the study. Ages range from 43 to 86 with a mean of $60\pm15$ years. All subjects were diagnosed as having ocular hypertension which, at the time of the experiment, did not warrant chronic therapy.

Verapamil was formulated from a 2.5 mg/ml intravenous solution (Searle Pharmaceuticals, Inc., Chicago, Ill.) by diluting it 1:1 with phosphate buffered saline, and adjusting the pH to 7.0. The final concentration was 1.25 mg/ml.

After a baseline measurement was taken by applanation tonometry, a 40 microliter drop of a 1.25 mg/ml solution of verapamil was instilled in one eye of each subject. After 30 minutes, a second IOP reading was taken. Blood pressure and pulse were monitored in some patients before and after the verapamil drop in order to determine if this calcium channel blocker may have cardiovascular side effects after ocular administration.

The patients described the sensations, e.g., comfort, etc., upon instillation and during the test period, as well as any other notable subjective effects.

The mean baseline pressure was $22.22\pm/-1.99$ OD and $23\pm/-4.8$ OS. After 30 minutes, seven of the nine volunteers has a significant drop in pressure in the verapamil treated eye. Also, six of the seven subjects who responded had a significant drop in IOP in the control eye. One subject who had no response in the verapamil-treated eye, had a drop in IOP of 4 millimeters Hg in the control eye. Another subject's IOP increased by one millimeter Hg in the verapamil-treated eye and decreased by one millimeter Hg in the control eye. The mean decrease in IOP in the verapamil-treated eye for all nine subjects was $-4.7$ millimeters Hg; in the control eye, $-2.6$ millimeters Hg. No effect on blood pressure or pulse was noted.

The data from this experiment are tabulated in Table 1 below, wherein all pressures are given in millimeters Hg.

TABLE 1

| Patient No. | Baseline | | | | 30 min after verapamil | | | | Change | |
|---|---|---|---|---|---|---|---|---|---|---|
| | OD | OS | B.P. | Pulse | OD | OS | B.P. | Pulse | (V) | (C) |
| 1 | 24 | 20 | 120/70 | 68 | 21(V) | 20(C) | 130/74 | 70 | −3 | 0 |
| 2 | 24 | 24 | 140/80 | 70 | 24(V) | 20(C) | 140/80 | 70 | 0 | −4 |
| 3 | 22 | 22 | 160/80 | 72 | 17(V) | 19(C) | 154/80 | 76 | −5 | −3 |
| 4 | 22 | 22 | 138/86 | 66 | 23(V) | 21(C) | 136/86 | 60 | +1 | −1 |
| 5 | 22 | 22 | 120/70 | 70 | 17(V) | 17(C) | 116/68 | 72 | −5 | −5 |
| 6 | 20 | 23 | NR | NR | 17(C) | 17(V) | NR | NR | −6 | −3 |

NR = not recorded

The results of this study indicated that verapamil is an effective agent for the treatment of ocular hypertension.

The invention having now been fully described, it should be understood that it may be embodied in other specific forms or variations without departing from its spirit or essential characteristics.

What is claimed is:

1. A method for lowering elevated intraocular pressure in a mammalian eye comprising administering to a mammalian eye having an elevated intraocular pressure an amount of a Class I calcium channel blocking agent effective to lower said elevated intraocular pressure.

2. The method of claim 1 wherein said mammalian eye is a human eye.

3. The method of claim 1 wherein said administration is topical administration directly to the eye.

4. The method of claim 3 wherein said effective amount is about 10 micrograms to about 1 milligram per eye per day.

5. The method of claim 3 wherein said calcium channel blocking agent is administered in solution in a pharmaceutically acceptable ophthalmic vehicle.

6. The method of claim 5 wherein said vehicle is comprised of saline solution.

7. The method of claim 6 wherein said vehicle contains from about 0.5 milligrams per milliliter to about 5 milligrams per milliliter of said calcium channel blocking agent.

8. The method of claim 1 wherein said Class I calcium channel blocking agent is verapamil.

* * * * *